United States Patent [19]

Chikama

[11] 4,332,242

[45] Jun. 1, 1982

[54] GUIDE TUBE ASSEMBLY

[75] Inventor: Toshio Chikama, Tokyo, Japan

[73] Assignee: Machida Endoscope Co., Ltd., Tokyo, Japan

[21] Appl. No.: 135,995

[22] Filed: Mar. 31, 1980

[51] Int. Cl.³ .............................................. A61B 1/00
[52] U.S. Cl. ........................................ 128/3; 128/348; 128/200.26
[58] Field of Search ....................... 128/200.26, 207.14, 128/207.17, DIG. 14, 348, 3, 4, 6; 138/DIG. 7

[56] References Cited

U.S. PATENT DOCUMENTS

| | | | |
|---|---|---|---|
| 2,607,342 | 8/1952 | Abel | 128/DIG. 14 |
| 3,667,781 | 6/1972 | Holbrook | 128/348 UX |
| 3,774,616 | 11/1973 | White et al. | 128/200.26 |
| 3,805,770 | 4/1974 | Okada | 128/4 |
| 3,963,856 | 6/1976 | Carlson et al. | 128/348 X |
| 4,082,893 | 4/1978 | Okita | 128/DIG. 14 X |

FOREIGN PATENT DOCUMENTS 2903049  8/1979  Fed. Rep. of Germany .......... 128/6

Primary Examiner—Paul J. Hirsch
Assistant Examiner—Mickey Yu
Attorney, Agent, or Firm—Berger & Palmer

[57] ABSTRACT

A guide tube assembly is disclosed which serves both as a guide tube for an endoscope and a suction tube for anesthesia. The guide tube assembly comprises a tube, said tube being made of a porous fluoric resin on which a fluorocarbon elastomer is coated for a sealing material, a mouthpiece which is a body of revolution, said mouthpiece comprising a connector portion for holding the tube, an extended portion which spreads from the connector portion and a mouthpiece portion. By these constructions, the assembly can be freely curved by the endoscope and effectively serves both as the guide tube for the endoscope and the anesthetic suction tube.

1 Claim, 4 Drawing Figures

GUIDE TUBE ASSEMBLY

BACKGROUND OF THE INVENTION

A. Field of the Invention

The present invention relates generally to an endoscopic technique or more particularly to a guide tube assembly which serves both as a guide tube for the endoscope and a suction tube for anesthesia.

B. Description of the Prior Art

An endoscope is an optical surgical instrument which utilizes flexible optical bundles and a flexible sheath for transmitting an image of an object caught at a forward end portion to an eyepiece assembly in a grip end. The endoscope is used for inspecting and treating a cancer and a polyp in a body cavity such as a bronchia and a stomach. When inserting the forward end portion and the flexible sheath into th body cavity for inspection and treatment, a guide tube is attached around the forward end portion and the flexible sheath so as to facilitate the insertion and prevent the wall of the body cavity from injury. In addition, the endoscope can be repeatedly inserted or pulled out by leaving the guide tube in a body cavity.

In an anesthetic operation, the endoscope is used for a manipulator of an anesthetic suction tube. For example, the suction tube is inserted into the bronchia with the aid of the endoscope and the anesthetic is introduced by way of the suction tube.

In the prior art, a silicon rubber tube is utilized for the guide tube of the endoscope. But, the cross section of the tube is easily deformed in the complicated body cavity and a friction resistance to the wall of the body cavity should not be disregarded, although the silicon tube is excellent in its flexibility. For the anesthetic suction tube, an integral molded tube made of PVC is widely used. But, the PVC tube is not so flexible, accordingly, the tube is difficult to be inserted into a desired position by the angle deflection mechanism of the endoscope. In addition, the PVC tube can not be sterilized in high-temperature after use. On the top of it, an anesthetic suction tube on which an olive oil is applied is used as guide tube means for both as the guide tube of the endoscope and the anesthetic suction tube. But, the guide tube means is difficult to be inserted into the desired position in the body cavity with the aid of the angle deflection means of the endoscope.

SUMMARY OF THE INVENTION

Accordingly, it is a primary object of the invention to obtain a guide tube assembly which serves both as a guide tube for the endoscope and the anesthetic suction tube.

It is another object of the invention to obtain the guide tube assembly which can be freely curved by the angle deflection means of the endoscope and be inserted in a desired position of the body cavity.

It is further object of the invention to obtain the guide tube assembly of low friction so that it can be smoothly inserted in the body cavity.

It is still further object of the invention to obtain the guide tube assembly which can be curved in the bronchia without deforming its cross section.

It is another object of the invention to obtain the guide tube assembly which can be repeatedly used by sterilizing it at high-temperature.

It is further object of the invention to obtain the guide tube assembly which is of low cost by exchanging its used tube.

To achieve the objects, the present invention is characterised in that it comprises a tube, said tube being made of a porous fluoric resin on which a fluorocarbon elastomer is coated for a sealing material and a mouthpiece which is a body of revolution.

The above and novel features of the invention will more fully appear from the following detailed description when the same is read in connection with the accompanying drawings. It is to be expressly understood, however, that the drawings are for purpose of illustration only and are not intended as a definition of the invention.

DETAILED DESCRIPTION OF THE PREFERRED EMBODIMENT

Figure 1:
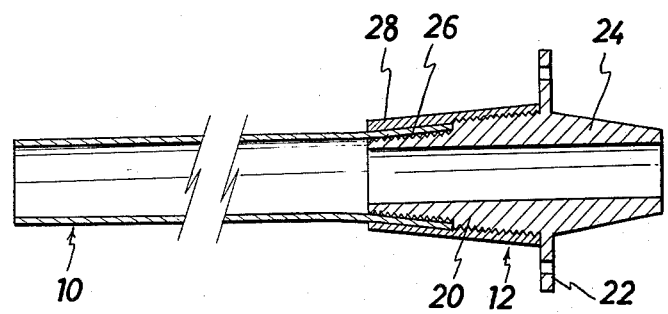
FIG. 1 is a cross-sectional view of a guide tube assembly according to one embodiment of the invention.
Figure 2:
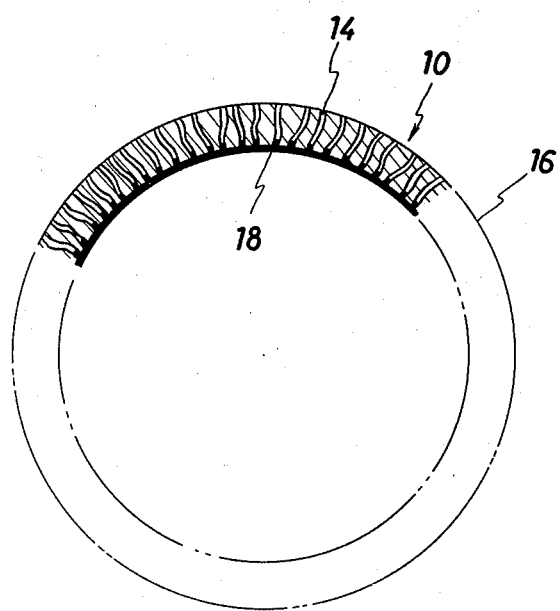
FIG. 2 is a cross-sectional view of a porous tube.
Figure 3:
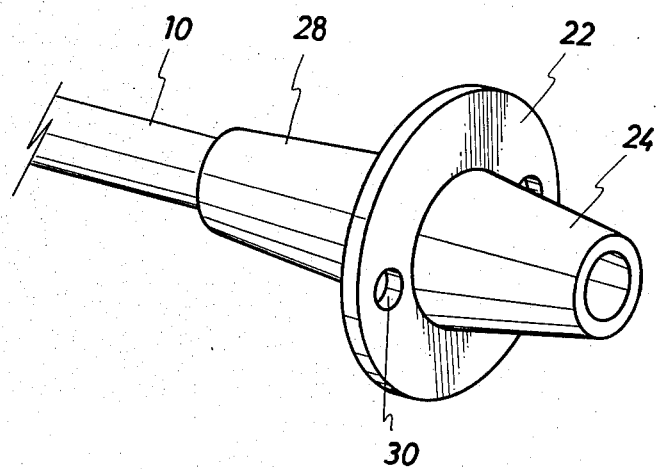
FIG. 3 is a perspective view of a mouthpiece.

Referring now to FIG. 1, numeral 10 indicates a tube and numeral 12 indicaes a mouthpiece. As shown in magnified scale in FIG. 2, the tube 10 is composed of a porous fluoric resin tube 16 which has numerous fine holes 14 in radial directions to its surface and a sealing material 18 of fluorocarbon elastomer which is coated on the porous tube 16. By way of Examples of the fluoric resin, polytetrafluor ethylene, polychlorotrifluor ethylene and polyfluorethylenepropylene may be adopted. For example of the fluorocarbon elastomer, copolymer of $CFCl=CF_2$ and $CH_2CF_2$ may be adopted. The porous fluoric resin tube 16 excedes in its flexibility and keeps its tublar cross section even when it is inserted in the complicated body cavity. Moreover, the tube 16 can be curved at will by the angle deflection mechanism of the endoscope. Further, the tube 16 can withstand at high temperature far more than 200°C., accordingly, it can be repeatedly used by sterilizing it after use. The sealing material 18 is for obtaining an airtightness of the tube 16. The material should be so provided that it barely permeates into the fine holes 14. The mouthpiece 12 of a body of revolution is made of metal or a plastic resin and comprises a connector portion 20 for holding one end of the tube 10, an extended portion 22 which spreads radially from the connector portion 20 and a mouthpiece portion 24 which is adjacent to the extended portion 22. A tapered screw 26 which is larger than the diameter of the tube 10 is provided at the connector portion 20. The tapered screw 26 is adopted so that the tube 10 may not be out of place, because it does not extend radially and has small friction coefficiency. The tube 10 is attached to the tapered screw 26 by twisting them together. A ring 28 is fitted in order that the tube 10 may be close together with the tapered screw 26. And the ring 28 is screwed to the connector portion 20. As shown in FIG. 3, one or a plurality of suction apertures 30 are provided at the extended portion 22 which spreads radially from the connector portion 20. The mouthpiece portion 24 for letting in the endoscope and the anesthetic is tapered and it may be connected with an anesthetic feeding apparatus (not shown).

In the next place, the operation of the guide tube assembly will be detailed hereinunder. In case that the assembly is utilized for the guide tube of the endoscope, the forward end portion and the flexible sheath is inserted into the tube 10 by way of the mouthpiece portion 24. And then, the forward end portion is covered by the assembly for letting it into the body cavity. After letting in the combination into the body cavity, the tube 10 can be freely curved and oriented by the angle deflector mechanism of the endoscope which comprises a deflector dial, wires and a succession of rings. By the mechanism, the forward end of the endoscope can be so oriented that the inspection and treatment of the body wall may easily be undertaken without injuring the wall. Moreover, the endoscope fully slides along the sealing material 18, accordingly, the endoscope can be repeatedly inserted into the tube 10. Further, the endoscope can be repeatedly inserted into the body cavity by way of the tube 10, as the tube 10 curves without deforming its cross section.

Figure 4:
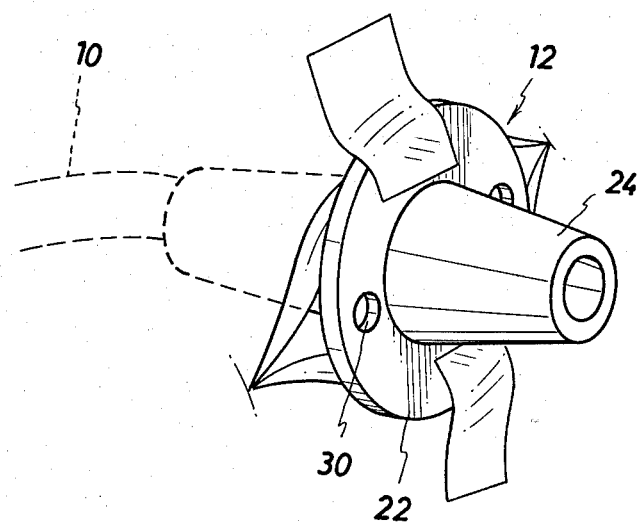
FIG. 4 is a perspective view showing how the guide tube assembly is used.

In the next place, I will describe the function of the guide tube assembly in case that it is used for an anesthetic suction tube. As to an emergency case by a traffic accident, for example, the patient can not swallow the anesthetic tube into the bronchia, because he may be unconscious. In addition, his mouth may be distorted by the accident, or a cramp and a clench may occur. In these cases, the guide tube assembly is introduced into a desired portion of the bronchia by the endoscope. In other words, the guide tube assembly according to the present invention can be inserted into the bronchia at will by the angle deflection mechanism of the endoscope. And, as shown in FIG. 4, the tube 10 is inserted into the bronchia and the mouthpiece is stopped at a mouth of the patient. The tube 10 can be freely curved in the bronchia, keeping its tubular cross section, for letting in the anesthetic precisely to the desired position. Moreover, the sealing material 18 of the tube 10 excedes in its air-tightness, so that the anesthetic may not be dissipated. Further, a saliva of the patient can be removed from the suction apertures 30 while in operation.

As described above, following effects can be obtained by the present invention. Firstly, the assembly can serve both as a guide tube for the endoscope and the suction tube for the anesthesia. Secondly, the tube can be freely curved in the complicated body cavity for inspection and treatment. Thirdly, the endoscope can be freely inserted into the tube, as the friction coefficient of the tube is small. Fourthly, the tube can be curved into the bronchia without deforming its tubular cross section. Fourthly, the tube can be repeatedly used by sterilizing it in high temperature after use. Fifthly, the guide tube is of low cost, as the tube can be exchanged.

While there have been shown and described and pointed out the fundamental novel features of the invention as applied to preferred embodiments. It will be understood, however, that the various omissions and substitutions and changes in the form and details may be made by those skilled in the art without departing from the spirit of the invention.

What is claimed is:

1. In combination, an endoscope and a guide tube assembly, said guide tube assembly comprising a tube, said tube being made of a porous fluoric resin and a fluorocarbon elastomer coated on said porous fluoric resin as a sealing material, said guide tube further comprising a mouthpiece which is formed as a surface of revolution comprising a connector portion for holding the tube, an extended portion which spreads from the connector portion and a mouthpiece portion, and at least one suction aperture being provided at the extended portion of the mouthpiece, wherein the surface of the mouthpiece portion is tapered, said endoscope passing through said tube, said tube formed of an inner surface of low friction.

* * * * *

UNITED STATES PATENT AND TRADEMARK OFFICE
CERTIFICATE OF CORRECTION

PATENT NO. : 4,332,242
DATED : June 1, 1982
INVENTOR(S) : Toshio Chikama

It is certified that error appears in the above-identified patent and that said Letters Patent is hereby corrected as shown below:

Title Page - Under "Filed: March 31, 1980" should read: -- [30]

Foreign Application Priority Data

April 12, 1979 [JP] Japan 54-048725--

Signed and Sealed this

Fourth Day of September 1984

[SEAL]

Attest:

GERALD J. MOSSINGHOFF

Attesting Officer

Commissioner of Patents and Trademarks